US009782608B2

(12) United States Patent
Qian et al.

(10) Patent No.: US 9,782,608 B2
(45) Date of Patent: Oct. 10, 2017

(54) HIGH INTENSITY FOCUSED ULTRASOUND TREATMENT HEAD AND SYSTEM

(75) Inventors: Min Kang Qian, Wuhan (CN); Yu Bei Hong, Wuhan (CN); Kan Rui, Wuhan (CN)

(73) Assignee: ANGEL SCIENCE & TECHNOLOGY (CANADA) INC., Toronto, ON (CA)

( * ) Notice: Subject to any disclaimer, the term of this patent is extended or adjusted under 35 U.S.C. 154(b) by 2126 days.

(21) Appl. No.: 11/620,575

(22) Filed: Jan. 5, 2007

(65) Prior Publication Data

US 2008/0167555 A1 Jul. 10, 2008

(51) Int. Cl.
*A61N 7/02* (2006.01)
*A61B 90/00* (2016.01)

(52) U.S. Cl.
CPC .......... *A61N 7/02* (2013.01); *A61B 2090/378* (2016.02)

(58) Field of Classification Search
CPC .............................. A61B 17/2258; A61B 8/00
USPC ............ 600/407, 437, 439, 459; 601/2, 3, 4
See application file for complete search history.

(56) References Cited

U.S. PATENT DOCUMENTS

| | | | |
|---|---|---|---|
| 4,771,787 A * | 9/1988 | Wurster et al. ................ | 600/439 |
| 4,932,414 A | 6/1990 | Coleman et al. | |
| 5,178,148 A | 1/1993 | Lacoste et al. | |
| 5,492,126 A * | 2/1996 | Hennige et al. ............... | 600/439 |
| 5,523,058 A | 6/1996 | Umemura et al. | |
| 5,722,411 A | 3/1998 | Suzuki et al. | |
| 5,762,066 A | 6/1998 | Law et al. | |
| 5,769,790 A | 6/1998 | Watkins et al. | |
| 5,984,881 A | 11/1999 | Ishibashi et al. | |
| 6,007,499 A * | 12/1999 | Martin et al. ..................... | 601/3 |
| 6,086,535 A | 7/2000 | Ishibashi et al. | |
| 6,267,734 B1 | 7/2001 | Ishibashi et al. | |
| 6,280,402 B1 | 8/2001 | Ishibashi et al. | |
| 6,425,867 B1 | 7/2002 | Vaezy et al. | |
| 6,488,639 B1 | 12/2002 | Ribault et al. | |
| 6,508,774 B1 | 1/2003 | Acker et al. | |
| 6,575,969 B1 | 6/2003 | Rittman, III et al. | |
| 6,626,855 B1 | 9/2003 | Weng et al. | |
| 6,666,833 B1 | 12/2003 | Friedman et al. | |
| 6,685,639 B1 | 2/2004 | Wang et al. | |
| 6,716,784 B2 | 4/2004 | Corma Canos et al. | |
| 6,790,187 B2 | 9/2004 | Thompson et al. | |
| 6,846,290 B2 | 1/2005 | Lizzi et al. | |
| 7,063,666 B2 | 6/2006 | Weng et al. | |
| 2008/0051656 A1* | 2/2008 | Vaezy et al. .................. | 600/439 |
| 2008/0275330 A1* | 11/2008 | Mu et al. ...................... | 600/411 |

* cited by examiner

*Primary Examiner* — Rochelle Turchen
(74) *Attorney, Agent, or Firm* — Patterson & Sheridan, L.L.P.

(57) ABSTRACT

The system comprises a therapeutic bed, a chamber, a combined head, a motional apparatus, a therapeutic power source, an imaging power source, a vacuum degassor, and a controller. The therapeutic transducer, the imaging transducer, and a rotator, together form the combined head. The combined head may also include an actuator. The rotator and actuator move the imaging transducer relative to the therapeutic transducer. The therapeutic transducer produces high intensity focused ultrasound, and treats target tissue in the body.

38 Claims, 5 Drawing Sheets

HIGH INTENSITY FOCUSED ULTRASOUND TREATMENT HEAD AND SYSTEM

BACKGROUND OF THE INVENTION

Field of the Invention

The present invention relates to high intensity focused ultrasound (HIFU), and a system for treatment using HIFU.

Description of the Related Art

Ultrasound

Sound waves are mechanical waves, typically generated by vibration, that propagate in a transmission medium such as air, water or human tissue. A sound wave may be categorized as follows based on its frequency:

- a sound wave less than the lower limit of human hearing, typically 16 Hz, is called an infrasonic wave or infrasound;
- a sound wave within the range of human hearing, typically from 16 Hz to 20 KHz, is called an acoustic wave; and
- a sound wave greater than the upper limit of human hearing, typically greater than 20 KHz, is called an ultrasonic wave or ultrasound;

Ultrasonic waves can transmit higher energy than acoustic waves. For example: a 1 MHz ultrasonic wave of the same amplitude as a 1 KHz acoustic wave transmits 100 times the energy. Ultrasound is ideal for applications requiring the transmission of large amounts of energy, though are often used in low energy applications as well.

In most systems, ultrasonic waves are generated by a piezoelectric material converting electrical energy to mechanical vibration and vice-versa. When vibration is induced on a piezoelectric material, an alternating voltage is produced between two surfaces of this material. This is the piezoelectric effect. Conversely, when alternating voltage is applied between two surfaces of this material, the material will vibrate with the same frequency as the alternating voltage being applied. This is called the inverse piezoelectric effect. A common piezoelectric material is quartz crystal, but there are many other piezoelectric materials. Typically, the piezoelectric elements that generate or receive ultrasonic energy are called transducers.

In some designs, an alternating current electric signal is applied to the opposite sides of the transducer. During the positive phase of the alternating voltage, the transducer is compressed, and during the negative phase of the alternating voltage, the transducer is stretched. When alternating electric signal is applied to the transducer surfaces, the transducer makes macroscopic deformations. The frequency of the vibrations is dictated by and matches the frequency of the alternating voltage signal. This movement produces ultrasound waves with the desired frequency.

Piezoelectric materials of different thickness or compositions may have different inherent resonance frequencies. When the frequency of an alternating electric signal matches the inherent resonance frequency of a transducer, the amplitude of vibration is greatest.

The distance that an ultrasonic wave transmits within one second is called the ultrasonic wave propagation velocity, or sound velocity. The ultrasonic sound velocity is different in different kinds of matter; and will change with changes in temperature, pressure and other factors.

When an ultrasonic wave is transmitted in the elastic medium, besides the pressure received when the system is at rest, the particles in the medium receive additional pressure p, alternating with time. We call the latter sound pressure, usually expressed in pascals. For a plain sound wave, it can be proved by the principle of acoustics that the amount of sound pressure may be expressed as:

$$p = \rho c \omega_A$$

In the equation, $\rho$ is the mass density of the medium, $\omega_A$ is the range of vibration velocity of the particle, c is the sound velocity. Since $\rho c$ is typically a physical constant of the sound medium, it is usually called the specific impedance of the medium, or simply the sound impedance, Z. The unit of Z is rayls.

$$1 \text{ rayls} = 1 \text{ g/cm}^2\text{s}$$

While discussing sound transmission, sound impedance is an extremely important physical quantity. If the Z value of the medium is constant throughout the medium in the direction of travel of the sound wave, the sound wave will not change its direction when transmitted in the medium, and will transmit forward constantly. In contrast, if the Z value of the medium is non-uniform, so-called acoustics interference will be shown at the variation position. According to terminology in acoustics interference, the sound wave will be reflected, refracted or scattered.

While the ultrasonic wave propagates in an elastic medium, the wave's energy attenuates. There are three typical causes of attenuation:

energy losses due to expansion of the wave front,
energy losses due to scattering, and
energy losses due to absorption in the medium.

The ultrasonic wave starts with a finite amount of energy. As the ultrasonic wave spreads, that energy is distributed over a larger wave front, weakening the effect of the wave at any given point. Focusing the ultrasound, as discussed below, can have the opposite effect in the focal region.

During the course of transmission of the ultrasonic wave, if it meets the acoustic impedance and a changing interface whose dimension is equal or smaller than the wavelength, a situation different from reflection will happen. A part of the acoustic energy is dispersed to all directions ("scattering"); the remaining acoustic energy continues spreading forward.

In common tap water, bubble and impurities in the water can cause scattering and make the ultrasonic energy attenuated. Therefore, de-aerated water is used in the ultrasonic treatment in order to reduce the scattering, so that more ultrasonic energy can reach the desired focus position. Similarly, the human body is made up of mediums (skin, fat, etc. . . . ) with different sound impedances, so as the sound wave travels through different tissue, some scattering will occur, which causes the wave energy to attenuate.

While the ultrasonic wave is transmitted in the tissue, its energy will also be absorbed constantly by the tissue as the wave propagates. There are at least a few principal mechanisms involved:

Viscous absorption: When the ultrasonic wave is transmitted in the tissue, vibration particles will have to overcome the viscous resistance of the particle, losing some energy in the process.

Heat conduction absorption: In the course of the transmission of sound waves, the positive and negative sound pressure in the medium will create cyclic diffusion. The temperature in positive sound pressure will rise, in negative sound pressure, the pressure will diffuse. Internal heat conduction will cause heat loss, consuming sound energy.

Molecular relaxation absorption: This is due to internal dynamics within the molecule of the medium. For instance, redistribution of the energy internal and external to the molecule, molecular structure change and chemical change, etc., can cause sound energy consumption.

The ultrasonic energy that the medium absorbs turns into heat energy, which increases the temperature. The sound intensity of the propagating wave decreases predictably as the propagation distance increases.

Current ultrasonic diagnosis imagery technology (such as b-scan diagnostic ultrasound) has been established on the foundation of the ultrasonic reflections and refractions (ultrasonic echo) from the human body. Its foundation is based on the fact that the acoustic impedance value of tissue is not uniform. Typically, when an organism suffers pathological change, its acoustic impedance value of the affected tissue changes, or the tissue itself move or changes shape, thus causing a corresponding change in the received ultrasonic echo. The ultrasonic echo thereby provides diagnostic information about pathological changes in a patient's tissue.

Ultrasonic Treatment

Over time, a number of methods to treat tissue with ultrasound have emerged. In the seventies, clinical physicians found that tumor cells are more sensitive to temperature than normal cells. Tumor cells die in abundance when their temperature is above 45 degrees Celsius. This early method of treatment irradiated the target region with a high-power ultrasonic wave while controlling the temperature at about 42 to 45 degrees Celsius accurately, through tissue temperature detection. With this early method, through electron focusing (or phased array focusing), the volume and shape of the target position is detected. All kinds of shapes can be regulated through electron focusing. This early method killed the tumor cells through long exposure (irradiation). Several systems of this design were developed in the last century.

Earlier systems had a number of drawbacks. Some of these earlier systems would take an unacceptably long time to treat the target tissue, which may require the patient to be sedated or otherwise immobilized to keep the target tissue still for the long periods of time required for treatment. Some of these earlier systems would require many hours of treatment to treat a large sized tissue mass.

Some early systems employing a phased array would generate harmonics that may create focused ultrasound outside of the focal point. A secondary harmonic may appear and damage tissue that is not an intended part of the treatment. Phased arrays also may have quality control and cost issues related to producing a completely consistent set of transducer elements. Minor variances in the characteristics of the transducer elements may produce ultrasound that is outside an acceptable range by hundreds or even thousands of Hz. Each transducer element has to be thoroughly checked for quality control, adding significantly to the cost of such a system. In addition, these minor variances between transducer elements may lead to difficulties in getting all the transducers in the array to fire simultaneously, to ensure that the resulting waves are properly in phase. Minor variances may cause the waves to be out of phase, degrading the performance of the phased array.

Researchers began to study the treatment of malignant tumors using heat at higher temperatures and more intense ultrasound, which lead to the development of a second method of ablating tissue using ultrasound therapy technology: HIFU technology.

In the 90's, HIFU research work started around the world. The HIFU treatment method generally involve generating an ultrasonic wave some distance away from the focal region, sometimes outside the patient's body, and focusing the HIFU energy (often measuring greater than one thousand watts per square centimeter ("W/cm$^2$")) at the target tissue inside the body, heating the target tissue rapidly to approximately 70 degrees Celsius or greater. The rapidly heated target tissue is ablated and destroyed, removing the threat that the target tissue may have posed.

High Intensity Focused Ultrasound

High Intensity Focused Ultrasound (HIFU) is one of the emerging medical treatment methods. HIFU is ultrasound in the range of approximately 0.2 MHz to 3.5 MHz, generated and focused to produce very high intensity sound at the focal point. The intensity of sound at the focal point can range from 500 W/cm$^2$ to upwards of 50 kW/cm$^2$.

During HIFU treatment, ultrasonic waves mainly produce the following four effects to tissue:

Heat effect: when ultrasound acts on tissue, it generates heat in the focal region. The tissue absorbs ultrasonic energy and converts it to heat, and in addition heat is generated by the reflection of ultrasonic waves on different surrounding tissues back on the target tissue. The heat effect is a basic mechanism of a HIFU treatment system. Temperatures in the focal region typically exceed 70° C.

Cavitation effect: under alternating sound pressure, the moisture in the target tissue cells in the focal region form tiny gas filled cavities or bubbles. Under high vibration intensity, the bubbles may explode, producing a shock wave that may cause a series of biochemical reactions and mechanical effects which in turn cause the destruction of the target cells.

Mechanical effect: the ultrasound mechanical vibrates the target tissue, which may affect the functional physiological processes and the whole structure of the cells in the acoustic field.

Immunoreaction: Research indicates that ultrasonic treatment to a tumor, can induce the immune response of the target tissue and weaken the tumor cells indirectly.

The target tissue may be a tumor or growth, fat cells, or any other type of biological matter within the body. Depending on the type of tissue and the desired effect, HIFU may be used to cut off blood flow to the target tissue, or destroy it altogether.

By using a therapeutic transducer, such as HIFU transducer shaped, or adapted with a lens, to direct the sound, the ultrasound beam may be concentrated on a focal region, resulting in maximum acoustical pressure concentrated in this region. A therapeutic transducer may also include a plurality of transducers elements all focused on the focal point, producing HIFU.

Tissue heating, cavitation, and the other effects are directly related to the acoustical pressure level. The highest level of acoustical pressure is in the focal region, and thus the consequent effects are most concentrated there. Due to these effects, a necrotic lesion is formed in the target tissue where the focal region lies.

In order for the HIFU system to work well, there are a number of considerations related to the treatment of tissue that need to be addressed.

The treatment method should kill the unwanted tissue without overly damaging the normal tissue around it.

The HIFU system should be able to change the location of the focal region, so that different types of treatments can be performed depending on where and what tissue is to be ablated. There is a need for a system that can minutely change the depth of the focal region. The depth is the distance of the focal region relative to the therapeutic head.

The HIFU system should be able to change to the angle at which it ablates tissue. Typically, the focal region defines volume of a known size and shape. The size and shape are determined by the characteristics of the HIFU transducer element. It is desirable to be able to manipulate the location of this volume in as many ways as practically possible, to minimize the risk of damage to normal tissue.

The HIFU system should be able to confirm the position and shape of the target tissue accurately. It is very important that the HIFU system targets and ablates only the target tissue, and not other tissue. The HIFU system, through computer and human oversight, should confirm the location and volume of the target tissue prior to treatment beginning on the body.

The HIFU system should be able to offer monitoring during treatment. The target tissue is not always fixed in place. The patient may move, or the treated tissue may shift the remaining target tissue during treatment. Also, the target tissue may require more treatment than originally scheduled in particular areas, and be instructed to do so as treatment progresses. Finally, it is important for safety reasons to confirm that the HIFU is focused precisely where it is supposed to be at all times.

Ultrasonic energy will attenuate while transmitting in tissue, due to heat losses and other effects. For this reason, treatment of target tissue located deep in the body requires that the HIFU system be able to generate high energy ultrasonic waves from the transducer, yet at the same time, it requires that the HIFU transducer focus the ultrasonic wave to a small focal region.

Some prior art systems use imaging systems, such as MRI or B-scan ultrasound, to confirm the position or shape of the target tissue before treatment. A few can monitor the treatment progress during treatment. U.S. Pat. No. 5,769,790 ("Watkins") discloses one way to monitor the treatment progress using an imaging transducer, such as a B-scan ultrasound, in a fixed position relative to the therapeutic head. Other prior art, such as U.S. Pat. No. 6,685,639 ("Wang") has the imaging transducer fixed beside or within the HIFU transducer to make up a therapeutic head. In each case, the imaging transducer is in a fixed position relative to the HIFU transducer, and focused where the focal region of the HIFU transducer is to be.

The problem with this approach is that the imaging transducer, typically B-scan ultrasound, being fixed relative to the HIFU transducer, is limited by its range of motion in what it can perceive before and during treatment. The B-scan ultrasound element images only a two dimensional plane, which does not reveal sufficient information about three dimensional structures in the body when fixed.

Operators of conventional handheld B-scan ultrasound units typically twist or rotate the handheld B-scan to get a sense of the topography of structures within the body. The rotation of a two dimensional scan can allow the operator to choose the most revealing two dimensional image, and gather information about the overall three dimensional structure.

Similarly, it is desirable to be able to vary the depth of the scan, so that the image produced shows detail about structures deeper within the body. On some patients, thick layers of fat or other tissue may obscure the target area. Operators of conventional handheld B-scan ultrasound units typically have to push the handheld B-scan into the body to get clear images of the structures deep within the body.

A system having the imaging transducer fixed to or incorporated into the HIFU element would have to rotate and push the entire head against the patient's body to capture clear images of some structures within the body, creating considerable discomfort. The HIFU element is typically a rigid element of considerable diameter, and pushing it against the patient's body is clearly undesirable.

Having an elongated imaging transducer that protrudes considerably into the field generated by the HIFU element may also be undesirable, as the imaging transducer may interfere with the transmission of the HIFU, and distort or degrade the strength and accuracy of the device.

The HIFU system should transmit the ultrasonic energy from the HIFU transducer into the body to the target tissue. Since it is well known that air is a relatively poor conductor for sound, deairated water is often used instead to propagate the sound from the HIFU transducer to the surface of the body with minimal and predictable energy losses. Any liquid with known sound transfer characteristics could be used, but deairated water is generally preferred, as its sound transfer characteristics are quite similar to that of living tissue. It is important that the HIFU system maintain water contact between the HIFU transducer and the body to prevent losses.

Some prior art systems use a bag to hold the deairated water and transmit the HIFU. This can be undesirable because a boundary layer of other material, such as the bag material, is placed either between the water and the body, or the HIFU transducer and the water, and scattering, diffraction, and heat losses occur at this boundary layer.

Some of the prior art uses an open ended bag, filled with deairated water, attached to the therapeutic head of the system. When the therapeutic head moves, it changes the volume enclosed by the open ended bag, and water is displaced out of the top of the bag. These changes in volume may lead to an air gap appearing between the body and the water, which would reduce the effectiveness of such a design.

It is necessary to have a system that prevents the appearance of such an air gap, without a boundary layer, and maintains direct contact between the deairated water and the body.

Many systems advocate either steady or pulsed HIFU in different patterns. Sustained HIFU of any significant duration may cause some discomfort or pain in patients, as the heating triggers nerve endings in the body to fire. It is desirable to have a method that minimizes discomfort from the heating.

There is a need to provide a HIFU system such as to remove or minimize the disadvantages mentioned above.

SUMMARY OF THE INVENTION

The invention relates to a combined head for the high intensity ultrasonic treatment of tissue comprising:
  a therapeutic transducer having a focal point, the therapeutic transducer capable of producing high intensity focused ultrasound;
  an imaging transducer having an axis, the axis passing through a point proximate to the focal point, and directed so that the focal point is within a scanning field of the imaging transducer, and the imaging transducer being rotatable, independent of therapeutic transducer, about the axis; and
  a rotator for rotating the imaging transducer about the axis.

The invention may include the combined head, wherein the imaging transducer is movable, independent of therapeutic transducer, along the axis, and comprising an actuator for moving the imaging transducer along the axis.

The invention relates to an ultrasound treatment system for the treatment of target tissue in a patient having skin using high intensity focused ultrasound comprising:
- a bed, the bed defining a hole in the top surface of the bed, the bed containing a chamber where the top of the chamber connects to the hole, the chamber filled with fluid;
- a combined head having:
    - a therapeutic transducer having a focal point, the therapeutic transducer capable of producing high intensity focused ultrasound, the transmitting face of the therapeutic transducer exposed to the chamber,
    - an imaging transducer having an axis, the axis passing through a point proximate to the focal point, and directed so that the focal point is within a scanning field of the imaging transducer, the imaging transducer being rotatable, independent of therapeutic transducer, about the axis, wherein the transmitting face of the imaging transducer is exposed to the chamber,
    - a rotator for rotating the imaging transducer about the axis;
- a multidirectional motional apparatus coupled to the combined head, the multidirectional motional apparatus allowing the motion of the head in at least three linear directions and in at least two rotational directions relative to the bed;
- a therapeutic power source connected to the therapeutic transducer for energizing the therapeutic transducer and generating high intensity focused ultrasound;
- an imaging power source connected to the imaging transducer for energizing the imaging transducer and producing a scanning field;
- a vacuum degasser connected to the chamber for degassing the fluid in the chamber;
- a controller connected to the multidirectional apparatus, the rotator, the therapeutic power source, the imaging power source, and the vacuum degasser, for controlling:
    - movement of the combined head through the multidirectional apparatus,
    - movement of the imaging transducer relative to the therapeutic transducer through the rotator,
    - energization of the imaging transducer through the imaging power source,
    - energization of the therapeutic transducer through the therapeutic power source, and
    - degassing of the fluid through the vacuum degasser,
- wherein the skin of the patient lying on the bed is in direct contact with the fluid in the chamber through the hole.

The invention may include the ultrasound treatment system, wherein the imaging transducer is movable, independent of therapeutic transducer, along the axis, the combined head comprises an actuator for moving the imaging transducer along the axis, the actuator is controlled by the controller, and the controller controls movement of the imaging transducer relative to the therapeutic transducer through the actuator.

The invention may include a method of applying high intensity focused ultrasound for the treatment of target tissue within the body, using a combined head having:
- a therapeutic transducer having a focal point, the therapeutic transducer capable of producing high intensity focused ultrasound, the transmitting face of the therapeutic transducer exposed to the chamber,
- an imaging transducer having an axis, the axis passing through a point proximate to the focal point and the imaging transducer, the imaging transducer directed so that the focal point is within its scanning field, the imaging transducer being rotatable, independent of therapeutic transducer, about the axis, wherein the transmitting face of the imaging transducer is exposed to the chamber, and
- a rotator for rotating the imaging transducer about the axis;

comprising the following steps:
- a) determining the size and location of the target tissue by:
    - i) scanning the target tissue from a first aspect, and capturing the outline of the target tissue,
    - ii) rotating the imaging transducer using the rotator, scanning the target tissue from a second aspect, and capturing the outline of the target tissue,
    - iii) moving the combined head to another location, scanning the target tissue, and capturing the outline of the target tissue, generating at least three captures,
    - iv) computing the size and location of the target tissue from the at least three captures;
- b) computing a treatment pattern; and
- c) treating the target tissue in accordance with the treatment pattern by:
    - i) moving the combined head to a position,
    - ii) activating the therapeutic transducer to treat tissue at the focal point,
    - iii) monitoring treatment progress in real time using the imaging transducer,
    - iv) repeating steps i to iii in accordance with the treatment pattern.

The invention may include the method described above, wherein step a) further comprises repeating steps a) i) to a) iii) to gather additional information regarding the size and location of the target tissue.

Other features of the invention will be evident from the disclosure of several embodiments that follows.

BRIEF DESCRIPTION OF THE DRAWINGS

Embodiments of the invention will be described by way of example and with reference to the drawings in which.

DETAILED DESCRIPTION

Figure 1:
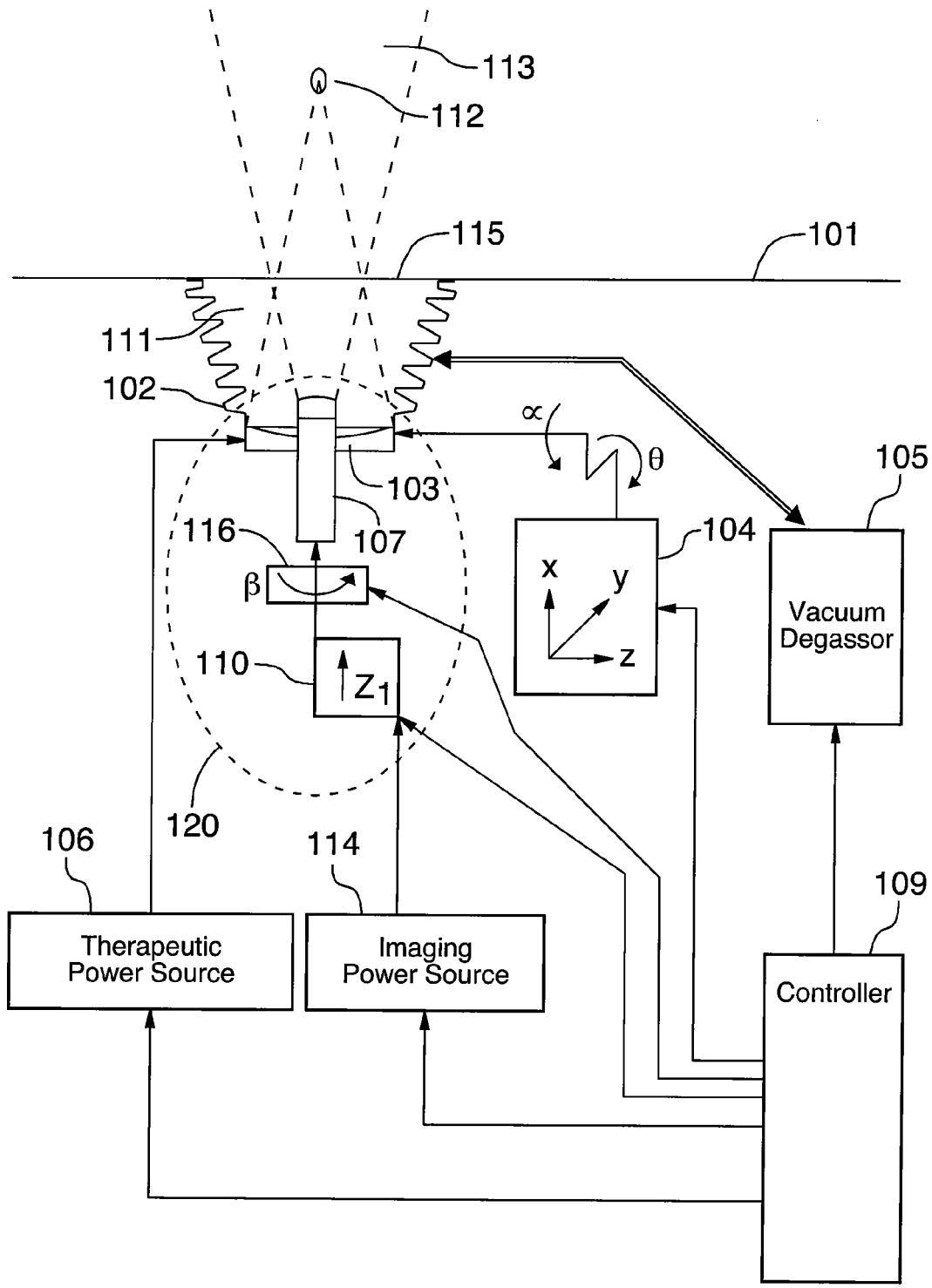
FIG. 1 is a schematic of the structure of an embodiment system according to the invention.

FIG. 1 is a schematic of the structure of the system according to the invention. The system comprises a therapeutic bed 101, a chamber 102, a combined head 120, a motional apparatus 104, a therapeutic power source 106, an imaging power source 114, a vacuum degassor 105, and a controller 109.

The therapeutic transducer 103, the imaging transducer 107, and a rotator 116, together form the combined head 120. The combined head 120 may also include an actuator 110.

The patient lies on the therapeutic bed 101, oriented to present the best access to the target tissue. Typically, but not always, this requires the patient to be placed with the skin closest to the target tissue over the hole 115 in the bed 101. The hole 115 is connected to a chamber filled with a fluid 111 having sound transmission characteristics similar to that of human tissue. Typically, the fluid 111 is degassed water which is gravity fed into the chamber from the vacuum degassor 105, as directed by the controller 109. In one embodiment, the fluid 111 is manually fed into the chamber 102 using a valve or a manual switch (not shown).

The chamber may be a flexible baffle 102 connected to the hole 115 and the combined head as depicted in this figure, or may be a larger chamber in which some or all of the motional apparatus 104 is also immersed in the fluid 111. It is important that at least the transmission faces of the therapeutic transducer 103 and the imaging transducer 107 are exposed to the fluid 111, but other parts may be partially or completely immersed, if waterproofed or if tolerant of the fluid 111.

In this embodiment, the bottom edge of the baffle 102 is coupled to the outside edge of the therapeutic transducer 103. The therapeutic transducer 103 produces a high intensity focused ultrasonic field with a focal point 112. Preferably, the imaging transducer 107 is mounted in the center of the therapeutic transducer 103 and directed to include the focal point 112 within its scanning field 113. The imaging transducer 107 may also be mounted off-center in the therapeutic transducer 103, or completely detached from the therapeutic transducer 103, so long as the imaging transducer 107 is directed to include the focal point 112 within its scanning field 113.

The combined head 120 is mounted on a multidirectional apparatus 104 which permits the movement of the combined head 120 in 3 dimensions, and also permits the orientation of the combined head 120 towards the target tissue. This may be achieved by permitting motion in the x, y, and z linear coordinate directions, and by permitting rotation of the combined head 120 in the α and θ rotational directions, where α and θ rotate about axes in a plane defined by the x and y linear directions. It is possible to conceive of other ways to achieve the same range of motion using a different set of dimensions.

The imaging transducer 107 is coupled to the rotator 116 which rotates the imaging transducer 107, independently of the therapeutic transducer 103, in the β rotational direction. If an actuator 110 is included, the actuator 110 is coupled to the imaging transducer 107 to permit motion of the imaging transducer 107 in the z1 linear direction. Note that the z1 and z linear directions do not necessarily align, depending on where the combined head 120 is located, and are completely independent.

The controller 109 is connected to the multidirectional apparatus 104, the actuator 110 (if present), the rotator 116, the therapeutic power source 106, the imaging power source 114, and the vacuum degasser 105. The controller 109 controls the combined head 120 movement through the multidirectional apparatus 104, the imaging transducer 107 movement relative to the therapeutic transducer 103 through the actuator 110 and the rotator 116, the energization of the imaging transducer 107 through the imaging power source 114, the energization of the therapeutic transducer 103 through the therapeutic power source 106, and the degassing of the fluid 111 through the vacuum degasser 105. The controller 109 may be comprised of computer hardware and software, and may be further divided or integrated with other components of the system.

Figure 2:
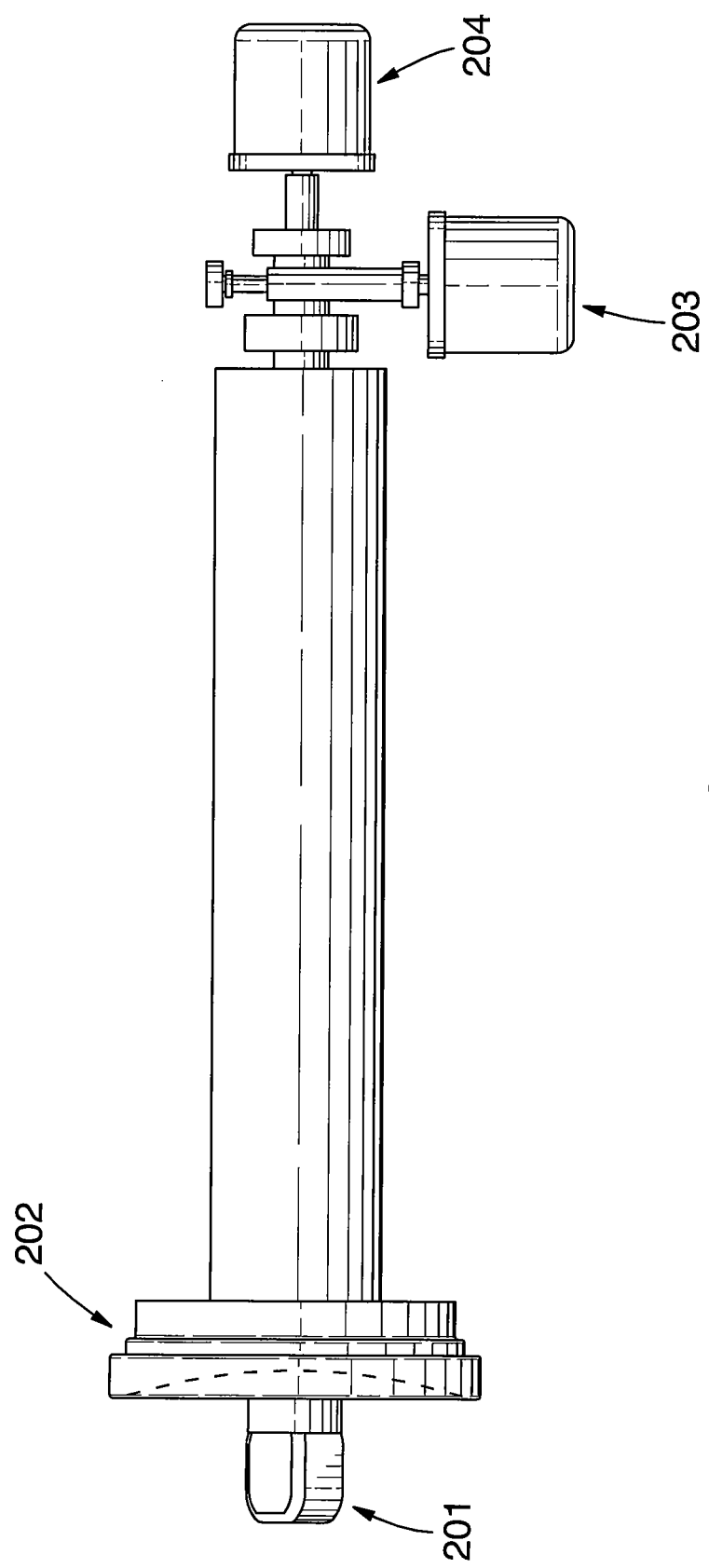
FIG. 2 is a schematic of the structure of an embodiment of the combined head according to the invention.

FIG. 2 is a schematic of the structure of an embodiment of the combined head according to the invention. The therapeutic transducer 202, the imaging transducer 201, and the rotator 204, together form the combined head. The combined head may also include the actuator 203. The therapeutic transducer 202, the imaging transducer 201, the rotator 204, and actuator 203 may be supported by a support structure, such as a housing.

The rotator 204 rotates imaging transducer 201 independently of the therapeutic transducer 202. The rotation of the imaging transducer assists in gathering information about the overall three dimensional structure of the target tissue.

The actuator 203, where included, moves the imaging transducer 201 independently of the therapeutic transducer 202 towards or away from the focal point, to aid in obtaining a clear image of structures deep within the body. In this embodiment, which incorporates the actuator 203, the imaging transducer 201 may be moved prior to treatment with the therapeutic transducer 202 to rest at or slightly below the surface of the therapeutic transducer 202, to reduce the possibility of imaging transducer 201 interfering with the HIFU produced by the therapeutic transducer 202.

Figure 3:
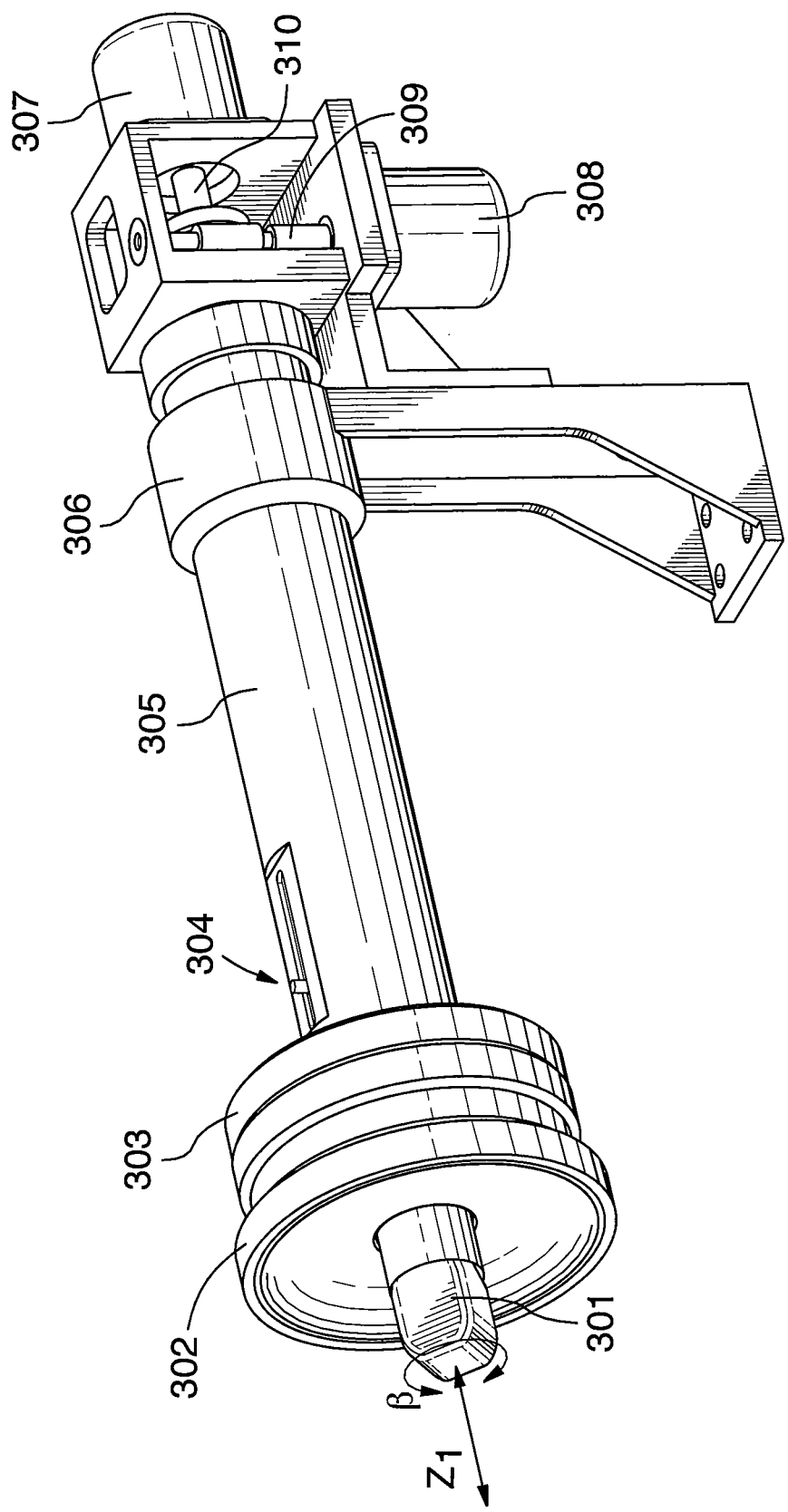
FIG. 3 is a detailed diagram of an embodiment showing the combined head and the desired movement of the combined head according to the invention.

FIG. 3 is a detailed diagram of an embodiment the combined head according to the invention. The elements of the combined head are contained within or mounted on a housing 305.

At one end of the housing 305, the therapeutic transducer 302, comprising a HIFU generating piezoelectric element, is mounted. In the centre of the therapeutic transducer 302, the imaging transducer 301 is passed through a hole in the therapeutic transducer 302, and housed partially within the housing 305. The imaging transducer 301, typically a B-scan ultrasound well known in the art, is aligned with the therapeutic transducer 302 so that the focal point of the therapeutic transducer 302 lies within the scanning field of the imaging transducer 301. The imaging transducer may be another medical scanning and imaging technology. The imaging transducer 301 is free to rotate within the housing 305, and free to slide within the housing 305.

In this embodiment, integral with the imaging transducer 301, there is a engagement mechanism 303 which permits the imaging transducer 301 to be attached to the chamber (not shown).

At the other end of the housing 305, the actuator and the rotator are mounted. In this embodiment, the actuator comprises a stepper motor 308 and a rack and pinion gear system 309 to convert the rotation from the motor into linear movement. In this embodiment, the rotator comprises a stepper motor 307 directly coupled through a coupling 310 to the imaging transducer 301. The actuator and the rotator could be comprised of hydraulic, pneumatic, magnetic, electromagnetic or other means of translating control signals to mechanical movement.

In this embodiment, the combined head is coupled to the rest of the system through a mounting bracket 306, attached to the housing 305. This embodiment includes a safety switch 304, which prevents the activation of the therapeutic transducer 302 if the imaging transducer 301 is mispositioned or overextended.

The imaging transducer 301 is coupled to the rotator which rotates the imaging transducer 301, independently of the therapeutic transducer 302, in the β rotational direction. The actuator is coupled to the imaging transducer 301 to permit motion of the imaging transducer 301 in the $z_1$ linear direction.

Figure 4:
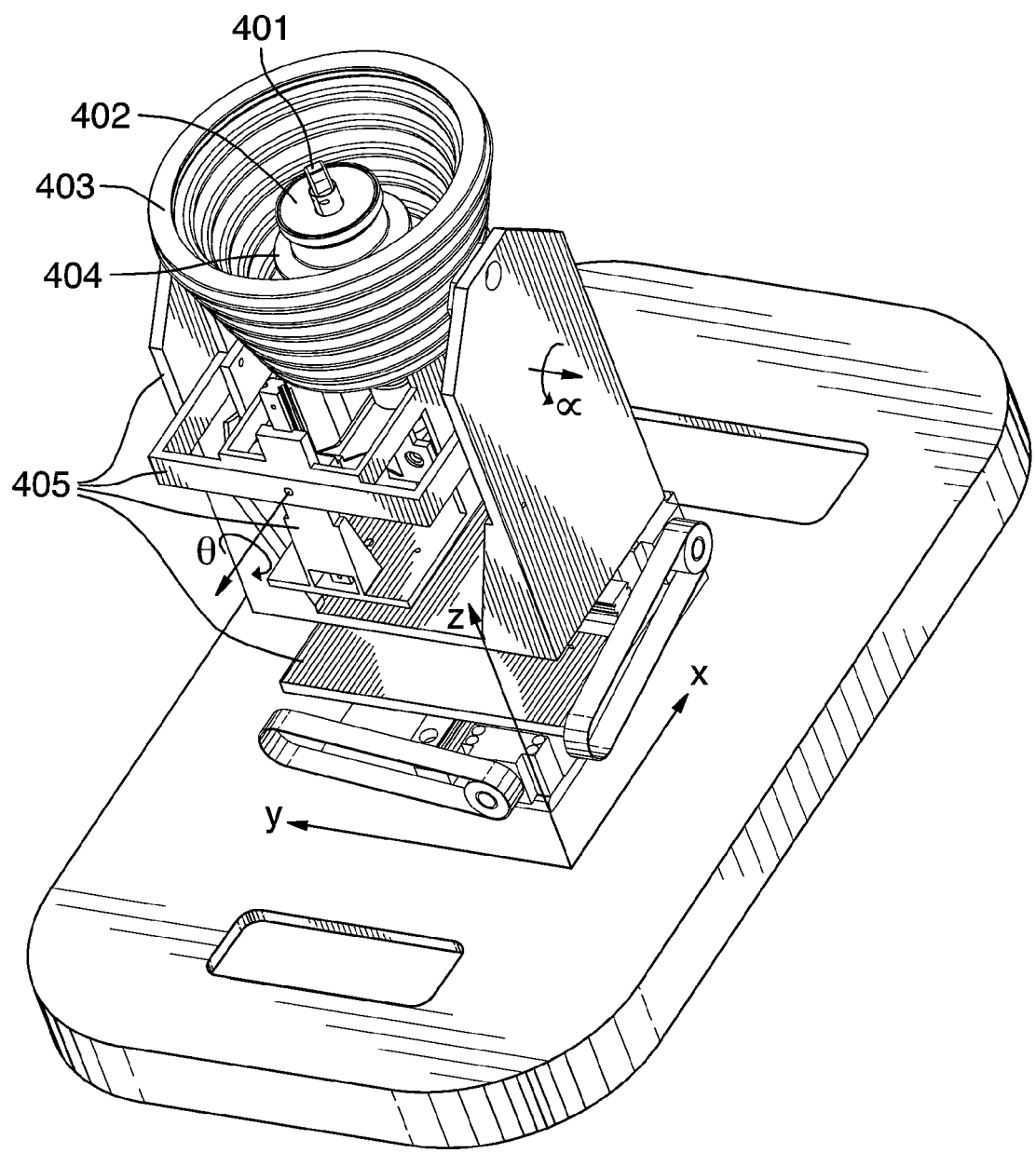
FIG. 4 is a schematic of the structure of an embodiment of the combined head and the motion apparatus according to the invention.

FIG. 4 is a schematic of the structure of an embodiment of the combined head and the motion apparatus according to the invention. In this embodiment, the combined head is mounted on a motional apparatus 405, which permits movement in three linear directions, x, y, and z, and in two rotational directions, α and θ. The chamber is comprised of a baffle 403 and an inner baffle 404.

The baffle 403 contains fluid, typically degassed water, and is attached along its upper edge to the bed (not shown). Along its lower edge, it is coupled to an inner baffle 404. The baffle 403 flexes along its sides to permit the motion of the combined head. As the baffle 403 swings to one side, that side compresses, but the opposite side expands, preserving the overall volume of the baffle 403, and reducing the tendency of the fluid contained within to be displaced out of the hole.

The inner baffle 404 is coupled along its upper edge to the therapeutic transducer 402, creating a seal along that edge. The transmission surfaces of the therapeutic transducer 402 and the imaging transducer 401 are exposed to the fluid. The inner baffle 404 flexes along its sides to permit vertical motion of the combined head. Using an inner baffle 404 is preferable to compressing the entire baffle 403, as a compression of the entire baffle 403 will tend to displace fluid out of the hole. The displacement caused by an elongation of the inner baffle 404 is comparatively much smaller, and may be accommodated by the elastic stretching of both baffles 403 404, and by minute stretching of the patient's skin when over the hole.

In an alternative embodiment of the invention (not shown), the combined head has a therapeutic transducer having a focal point and a transmitting face exposed to the chamber, and an imaging transducer having an axis and a transmitting face, the axis passing through a point proximate to the focal point and directed so that the focal point is within the scanning field of the imaging transducer and the transmitting face is exposed to the chamber. The combined head also has a rotator for rotating the imaging transducer about the axis and a support structure coupled to the therapeutic transducer, the imaging transducer, and the rotator.

In this embodiment, the imaging transducer is movable independently of the therapeutic transducer along the axis by an actuator in the combined head towards or away from the focal point. The actuator is controlled by the controller, and the controller controls movement of the imaging transducer relative to the therapeutic transducer through the actuator.

In this embodiment, the chamber is comprised of a baffle, a first inner baffle, and a second inner baffle. Similar to the baffle 403 of FIG. 4, the baffle contains fluid, typically degassed water, and is attached along its upper edge to the therapeutic bed. Along its lower edge, it is coupled to a first inner baffle and a second inner baffle. The first inner baffle is coupled along its lower edge to the baffle and is coupled along its upper edge to the border of the transmitting face of the therapeutic transducer, creating a seal along that edge. The transmission surface of the therapeutic transducer is exposed to the fluid. The second inner baffle is coupled along its lower edge to the baffle and is coupled along its upper edge to the border of the transmitting face of the imaging transducer to form an upper edge coupling that permits rotation of the imaging transducer. The transmission surface of the imaging transducer is exposed to the fluid. The second inner baffle flexes along its sides to permit vertical motion of the imaging transducer.

Figure 5:
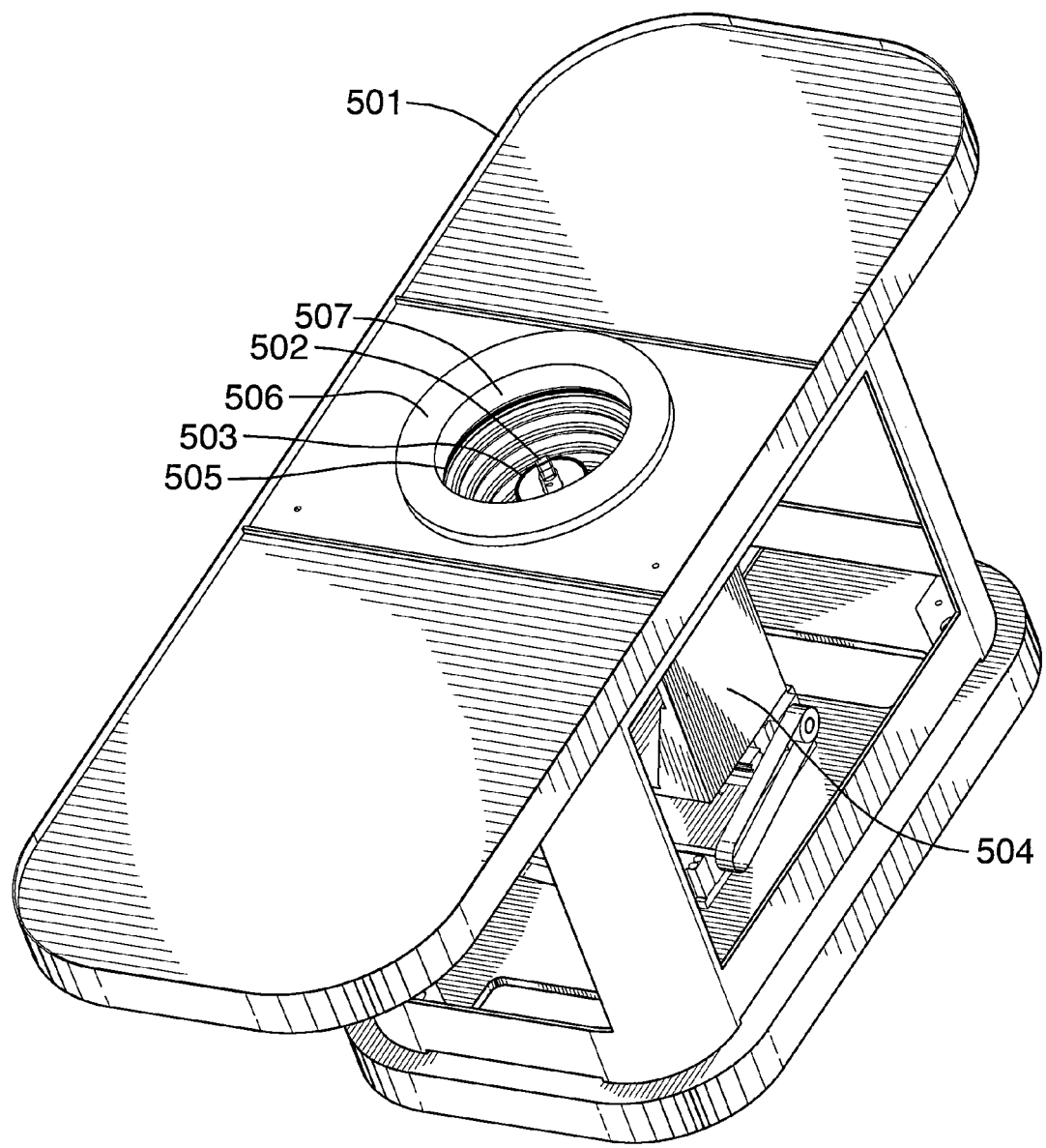
FIG. 5 is a schematic of the structure of an embodiment of the combined head and the motion apparatus of the invention in the therapeutic bed according to the invention.

FIG. 5 is a schematic of the structure of an embodiment of the combined head and the motion apparatus of the invention in the therapeutic bed according to the invention. The bed 501 may be of any size and shape that accommodates the patient. The bed 501 defines a hole 507, over which the target tissue is positioned. The top edge of the baffle 505 is attached to the hole 507.

The bed 501 may comprise a cushion 506 placed around the hole 507, which may provide a better seal with the baffle 505 to contain the fluid, and may make the patient more comfortable.

The combined head, comprising the imaging transducer 502, the therapeutic transducer 503, the rotator (not shown), and the actuator (not shown), resides in the hole 507, contained within the baffle 505. The motional apparatus 504 may be accommodated underneath the bed 501.

Therapy may proceed by any number of methods. The basic steps of any method of treatment with this device include the following basic steps:
  determining the size and position of the target tissue using the imaging transducer,
  developing a treatment pattern, and
  treating the target tissue with the therapeutic transducer in accordance with the treatment pattern.

The determination of the size and position of the target tissue may be achieved by scanning the target tissue from a number of different positions relative to the target tissue, and from a number of different aspects in each position. The aspect is changed by rotating the imaging transducer using the rotator, and by changing the distance of the imaging transducer from the target tissue using the actuator.

Each scan of the target tissue produces an image, which is then assessed by the system with the assistance of a human operator to outline the target tissue on the image. Each outline is referred to as a capture of the target tissue. The system compares at least three of these captures to produce a detailed virtual three dimensional model of the target tissue. Methods to convert a number of two dimensional images taken from known perspectives into a three dimensional volume are well known in the art.

According to the shape of the target tissue, the system, with assistance of a human operator, may plan a treatment pattern that will specify the movement and orientation of, and the number and length of pulses produced by, the therapeutic transducer.

For example, it may be desirable to destroy an entire volume of target tissue, in which case the treatment plan may simply specify passing from point to point to destroy a line of tissue, from line to line to destroy an area of tissue, and from area to area to destroy a volume of tissue.

In other cases, it may be desirable to cut off blood flow to a particular area, in which case the treatment plan may ablate only specified areas of tissue to achieve the desired effect.

Once a treatment plan is established, the system may treat the target tissue in accordance with the treatment plan. This may involve moving the combined head to a specified position, activating the therapeutic transducer to producing one or more pulses of HIFU energy that converge at the focal point and destroy the tissue there, monitoring the effects of the HIFU on the target tissue in real time using the imaging transducer, and then repeating the above steps until the treatment plan is complete and the target tissue is destroyed. The treatment plan may be altered during the course of treatment on the basis of the realtime feedback from the imaging transducer.

In a preferred embodiment, the pulses of energy produced by the therapeutic transducer are extremely intense and short, less than 0.3 seconds in length, and typically between 0.1 to 0.3 seconds in length. The extremely short bursts destroy the target tissue within a short time by rapidly raising the temperature of the target tissue to above 70 degrees Celsius. The extremely short bursts reduce the discomfort that the patient feels, and allow the procedure to be carried out with the patient conscious and alert, and in a much shorter time period than previous systems. The patient may still feel a dull ache for a short time after the treatment, depending on the individual patient's sensitivity.

The invention claimed is:

1. A combined head for high intensity ultrasonic treatment of tissue, the combined head coupled to a motional apparatus as part of a system that generates high intensity ultrasound, the combined head comprising:
   a. a therapeutic transducer having a focal point, the therapeutic transducer capable of producing high intensity focused ultrasound;
   b. an imaging transducer having an axis, the axis passing through a point within a scanning field of the imaging transducer and proximate to the focal point, and directed so that the focal point is within the scanning field of the imaging transducer, and the imaging transducer being rotatable, independent of the therapeutic transducer, about the axis;
   c. a rotator for rotating the imaging transducer about the axis; and
   d. a support structure coupled to the therapeutic transducer, the imaging transducer, and the rotator,
   wherein the motional apparatus is configured to move the combined head, in three spatial dimensions to cause both the therapeutic transducer and the imaging transducer to move together in three spatial dimensions relative to a patient, and the movement of the combined head causes the focal point to move to a plurality of positions within the patient, and
   wherein the therapeutic transducer is activated while the focal point is at each position to destroy the tissue located at each position.

2. The combined head of claim 1, wherein the imaging transducer is movable, independent of therapeutic transducer, along the axis, and comprising an actuator for moving the imaging transducer along the axis, the actuator coupled to the support structure.

3. The combined head of claim 1, wherein the therapeutic transducer is a single hemispherical transducer.

4. The combined head of claim 1, wherein the therapeutic transducer is a HIFU transducer adapted with a lens, focused on the focal point.

5. The combined head of claim 1, wherein the therapeutic transducer is a plurality of HIFU transducers focused on the focal point.

6. The combined head of claim 1, wherein the axis passes through the therapeutic transducer.

7. The combined head of claim 6, wherein the therapeutic transducer defines a hole along the axis sized to permit passage of the imaging transducer therethrough.

8. The combined head of claim 1, wherein the imaging transducer is a B-scan ultrasound transducer.

9. The combined head of claim 1, wherein the rotator comprises a stepper motor coupled to the imaging transducer.

10. The combined head of claim 2, wherein the actuator comprises a stepper motor coupled to a gear system, the gear system designed to translate rotational motion into linear motion.

11. The gear system of claim 10, wherein the gear system is in a rack and pinion configuration.

12. The combined head of claim 2 comprising a safety switch preventing the generation of high intensity focused ultrasound by the therapeutic transducer when the imaging transducer is improperly positioned.

13. The combined head of claim 2, wherein the axis passes through the therapeutic transducer.

14. The combined head of claim 13, wherein therapeutic transducer defines a hole along the axis, though which the imaging transducer may pass.

15. An ultrasound treatment system for the treatment of target tissue using high intensity focused ultrasound comprising:
   a. a bed, the bed defining a hole in a top surface of the bed, the bed containing a chamber connected to the hole through a common passageway, the chamber being filled with a fluid;
   b. a combined head having:
      i. a therapeutic transducer having a focal point and a transmitting face, the therapeutic transducer capable of producing high intensity focused ultrasound, the transmitting face of the therapeutic transducer being exposed to the chamber,
      ii. an imaging transducer having an axis and a transmitting face, the axis passing through a point within a scanning field of the imaging transducer and proximate to the focal point, and directed so that the focal point is within the scanning field of the imaging transducer, the imaging transducer being rotatable, independent of the therapeutic transducer, about the axis, wherein the transmitting face of the imaging transducer is exposed to the chamber,
      iii. a rotator for rotating the imaging transducer about the axis, and
      iv. a support structure coupled to the therapeutic transducer, the imaging transducer, and the rotator;
   c. a multidirectional motional apparatus coupled to the combined head, the multidirectional motional apparatus being configured to move the head in at least three linear directions to cause both the therapeutic transducer and the imaging transducer to move together in three spatial dimensions relative to a patient, and to move the head in at least two rotational directions relative to the bed wherein the motional apparatus moves the combined head, and the movement of the combined head causes the focal point to move to a plurality of positions within the patient, wherein the therapeutic transducer is activated while the focal point is at each position to destroy the tissue located at each position;
   d. a therapeutic power source connected to the therapeutic transducer for energizing the therapeutic transducer and generating high intensity focused ultrasound;
   e. an imaging power source connected to the imaging transducer for energizing the imaging transducer and producing a scanning field;
   f. a vacuum degasser connected to the chamber for degassing the fluid in the chamber;
   g. a controller connected to the multidirectional apparatus, the rotator, the therapeutic power source, the imaging power source, and the vacuum degasser, for controlling:
      i. movement of the combined head through the multidirectional motional apparatus,
      ii. movement of the imaging transducer relative to the therapeutic transducer through the rotator,
      iii. energization of the imaging transducer through the imaging power source,
      iv. energization of the therapeutic transducer through the therapeutic power source, and
      v. degassing of the fluid through the vacuum degasser.

16. The ultrasound treatment system of claim 15, wherein the imaging transducer is movable, independent of the therapeutic transducer, along the axis, the combined head comprises an actuator for moving the imaging transducer along the axis, the actuator is controlled by a controller, and the controller controls movement of the imaging transducer relative to the therapeutic transducer through the actuator.

17. The ultrasound treatment system of claim 15, wherein the therapeutic transducer is a single hemispherical transducer.

18. The ultrasound treatment system of claim 15, wherein the axis passes through the therapeutic transducer.

19. The ultrasound treatment system of claim 18, wherein therapeutic transducer defines a hole along the axis, though which the imaging transducer may pass.

20. The ultrasound treatment system of claim 15, wherein the imaging transducer is a B-scan ultrasound transducer.

21. The ultrasound treatment system of claim 15, wherein the rotator comprises a stepper motor coupled to the imaging transducer.

22. The ultrasound treatment system of claim 15, wherein the fluid is gravity fed into the chamber from the bottom of the chamber to minimize cavitation.

23. The ultrasound treatment system of claim 15, wherein the controller comprises one or more subcontrollers for controlling separately or in combination any of the multidirectional apparatus, the actuator, the rotator, the therapeutic power source, the imaging power source, and the vacuum degasser.

24. The ultrasound treatment system of claim 15, wherein the controller comprises a manual controller for controlling the flow of fluid into and out of the chamber.

25. The ultrasound treatment system of claim 16, wherein the axis passes through the therapeutic transducer.

26. The ultrasound treatment system of claim 25, wherein therapeutic transducer defines a hole along the axis sized to permit passage of the imaging transducer therethrough.

27. The ultrasound treatment system of claim 16, wherein the actuator comprises a stepper motor coupled to a gear system, the gear system designed to translate rotational motion into linear motion.

28. The ultrasound treatment system of claim 27, wherein the gear system is in a rack and pinion configuration.

29. The ultrasound treatment system of claim 16, the combined head having a safety switch preventing the generation of high intensity focused ultrasound by the therapeutic transducer when the imaging transducer is improperly positioned.

30. The ultrasound treatment system of claim 16, wherein the chamber comprises a baffle, the baffle being elastic.

31. The ultrasound treatment system of claim 16, wherein the chamber comprises:
  a. a baffle, the baffle being elastic, and
  b. an inner baffle having an upper edge and a lower edge, the inner baffle being elastic, the inner baffle coupled along its upper edge to the border of the transmitting face of the therapeutic transducer, and the inner baffle coupled along its lower edge to the baffle.

32. The ultrasound treatment system of claim 16, wherein the chamber comprises:
  a. a baffle, the baffle being elastic, and
  b. a first inner baffle having an upper edge and a lower edge, the first inner baffle being elastic, the first inner baffle coupled along its upper edge to the border of the transmitting face of the therapeutic transducer, and the first inner baffle coupled along its lower edge to the baffle, and
  c. a second inner baffle having an upper edge and a lower edge, the second inner baffle being elastic, the second inner baffle coupled along its upper edge to the border of the transmitting face of the imaging transducer to form an upper edge coupling, and the second inner baffle coupled along its lower edge to the baffle, wherein the upper edge coupling permits rotation of the imaging transducer.

33. A method of applying high intensity focused ultrasound for the treatment of target tissue within the body, using a combined head having:
  a therapeutic transducer having a focal point and a transmitting face, the therapeutic transducer capable of producing high intensity focused ultrasound, the transmitting face of the therapeutic transducer exposed to a chamber,
  an imaging transducer having an axis and a transmitting face, the axis passing through a point within a scanning field of the imaging transducer and proximate to the focal point, and directed so that the focal point is within the scanning field of the imaging transducer, the imaging transducer being rotatable, independent of therapeutic transducer, about the axis, wherein the transmitting face of the imaging transducer is exposed to the chamber, and
  a rotator for rotating the imaging transducer about the axis;
the method comprising the following steps:
  a. determining the size and location of the target tissue by:
    i. scanning the target tissue from a first aspect, and capturing the outline of the target tissue,
    ii. rotating the imaging transducer using the rotator, scanning the target tissue from a second aspect, and capturing the outline of the target tissue,
    iii. moving the combined head to another location, scanning the target tissue, and capturing the outline of the target tissue, generating at least three captures,
    iv. computing the size and location of the target tissue from the at least three captures;
  b. computing a treatment plan; and
  c. treating the target tissue in accordance with the treatment plan by:
    i. moving the combined head in three spatial dimensions to cause both the therapeutic transducer and the imaging transducer to move together in three spatial dimensions relative to a patient, which causes the focal point to move to a position specified in the treatment plan,
    ii. activating the therapeutic transducer to destroy the tissue at the focal point by heating it,
    iii. monitoring treatment progress in real time using the imaging transducer,
    iv. repeating steps i to iii in accordance with the treatment plan to destroy an entire volume of the tissue.

34. The method of claim 33, wherein step (a) further comprises repeating steps (a)(i) to (a)(iii) until sufficient additional information regarding the size and location of the target tissue is gathered to generate a 3-D model of the target tissue.

35. The method of claim 33, wherein the imaging transducer is movable, independent of therapeutic transducer, along the axis, and the combined head comprises an actuator for moving the imaging transducer along the axis, and wherein step (a) further comprises actuating the actuator to move the imaging transducer along the axis.

36. The method of claim 35, wherein step (c) further comprises actuating the actuator to move the imaging transducer along the axis out of the HIFU field generated by the therapeutic transducer.

37. The method of claim 33, wherein the activation of the therapeutic transducer in step (c)(ii) has a duration of less than 0.3 seconds.

38. The method of claim 33, wherein step (a)(iii) further comprises altering the treatment plan in response to real-time information gathered under step (c)(iii).

* * * * *